United States Patent [19]

Carde et al.

[11] 4,010,255

[45] Mar. 1, 1977

[54] SEX PHEROMONE FOR POTATO TUBEWORM MOTH, *PHTHORIMEA OPERCULELLA*

[75] Inventors: Ring T. Carde; Jan P. Kochansky; Wendell L. Roelofs, all of Geneva, N.Y.

[73] Assignee: Cornell Research Foundation, Inc., Ithaca, N.Y.

[22] Filed: June 19, 1975

[21] Appl. No.: 588,343

[52] U.S. Cl. .............................. 424/84; 260/488 H
[51] Int. Cl.² ........................................ A01N 17/14
[58] Field of Search ................... 424/84; 260/488 H

[56] References Cited

UNITED STATES PATENTS 3,845,108   10/1974   Roelofs et al. ................ 260/488 H

OTHER PUBLICATIONS

Chemical Abstracts, vol. 77 (1972), p. 110559m.
Chemical Abstracts, vol. 79 (1973), p. 113354t.

*Primary Examiner*—V. D. Turner
*Attorney, Agent, or Firm*—Lawrence E. Laubscher; Ralph R. Barnard; Theodore C. Wood

[57] ABSTRACT

A compound was isolated from female *Phthorimea operculella* (*Lepidoptera: Gelechiidae*) extracts and identified as trans-4, cis-7-tridecadienyl acetate. The compound was then synthesized. This compound elicits good male *P. operculella* responses in laboratory and field assays. The corresponding alcohol also appeared to be present in the female glands, but was not found to increase male responses in the laboratory or the field.

3 Claims, 1 Drawing Figure

SEX PHEROMONE FOR POTATO TUBEWORM MOTH, *PHTHORIMEA OPERCULELLA*

BACKGROUND OF THE INVENTION

In recent years, the ecological problems raised by the widespread use of certain insecticides, in particular halogenated aromatics such as DDT, have initiated the search for more specific methods of destroying insect pests, which, if they do not entirely eliminate the use of such harmful insecticides as pesticides, at least considerably cut down on the area in which they are broadcast. One mode which has been found of great interest in recent years has been the use of sex attractants or pheromones to attract either the male or the female of a particular species or a number of species to a particular and small location where they can be destroyed thereby interrupting the breeding cycle and cutting down the number of such pests in the next season. One technique employed for this purpose is to isolate either the male or the female pheromone and insert it into an insect trap which is then located in the area which it is desired to protect from a particular species of moth or other insect. The vapor from the trap attracts the insects into the trap where they are either held or killed, thus removing them from the general populace. Another mode which has been found of great interest has been the use of sex attractants or pheromones by permeating the air over the infested area for mating disruption.

SUMMARY OF THE INVENTION

The potato tuberworm, *Phthorimea operculella* (Zeller), is a key pest of potato in many areas of the world. The sex pheromone of this species includes a compound which provides a potent population monitoring system and permits mating disruption programs for this insect. An unusual odd-carbon-chain structure trans-4, cis-7-tridecadienyl acetate was identified as a pheromone compound for this species and that compound was synthesized.

DESCRIPTION OF THE PREFERRED EMBODIMENT

Figure 1:
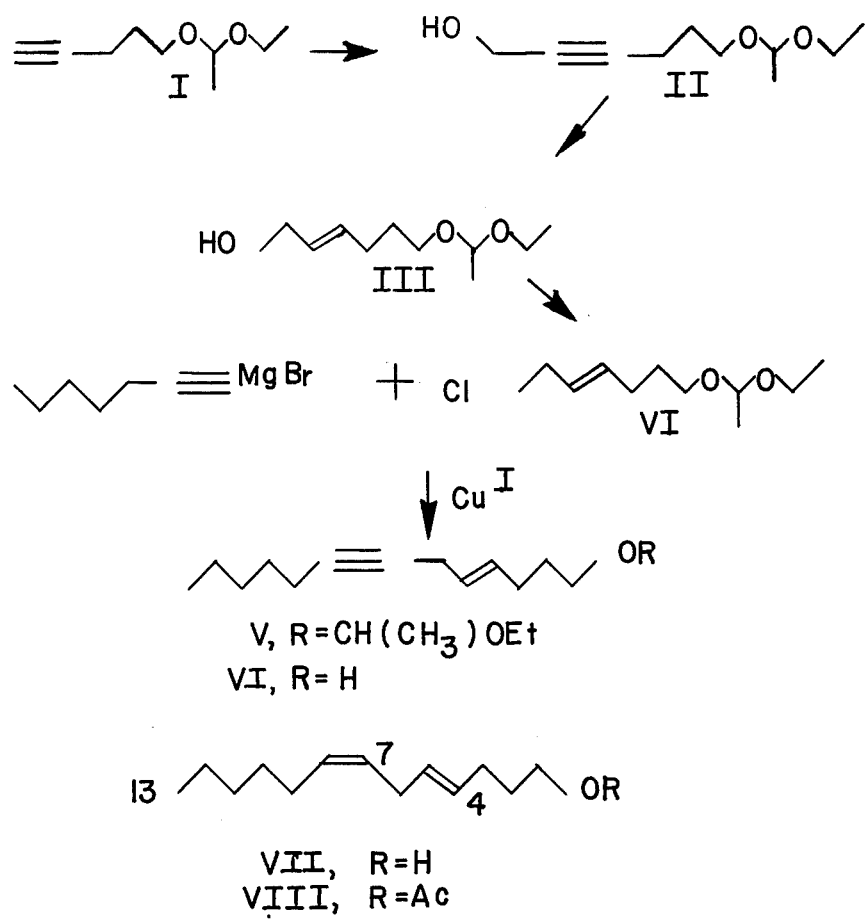

Various materials and methods (A) are preferably employed to extract the sex pheromone from the female potato tuberworm, to identify the active compounds in the pheromone (B), to synthesize the active compounds (C) and to test the male behavioral responses (D) to the synthetic compounds.

(A) Materials and Methods

*P. operculella* were obtained from laboratory cultures maintained on potatoes under a 16 hr photophase regime at 25° C. Pupae were segregated by sex and held along with emergent adults in separate rearing chambers. The abdominal tips of 2-3 day-old females were excised during the 3.5 to 5th hr of scotophase and extracted with methylene chloride.

Gas chromatographic columns (glass, 2 m × 4 mm) were packed with OV-1 (3% methyl silicone) XF-1150 (10% cyanoethyl [50%], methyl silicone, or CHDMS (3% cyclohexanedimethanol succinate) - all on 100-120 mesh Gas-Chrom A, and 3% Carbowax 20M on 100-120 mesh Chromosorb W. A preparative column (glass, 2.5 m × 8 mm) of SE-30 (5% methyl silicone on 60-80 mesh Gas-Chrom Z) was also used. High pressure liquid chromatography was carried out on a 2 × 6 mm stainless steel column packed with Bio-Beads SX-2 (Bio-Rad Laboratories) and eluted with benzene at 1 ml/min. Mass spectra were obtained at the Cornell Mass Spectrometry Facility with a Finnigan GC/MS using an OV-1 column. Electroantennograms (EAG) were run for assaying gas chromatographic collections of female tip extracts and for plotting response profiles with long-chain acetates, alcohols and aldehydes. A method of producing EAG is described in *J. Insect Phisiol.* 17, 1969–1982(1971) by W. Roelofs and A. Comeau. A method for assaying gas chromatographic collections of female tip extracts is described in *Science* 174, 297–299 (1971) by W. Roelofs, A. Comeau, A. Hill, and G. Milicevic. A method for plotting response profiles with long-chain acetates, alcohols and aldehydes is described in *J. Chem. Ecol.* 1 91–99 (1975) by A. Hill and W. Roelofs.

Behavioral response assays were conducted using glass tubes 1.7 cm ID × 88 cm, screened at each end. The use of glass tubes to conduct such assay is described in *Ann. Entomol. Soc. Amer.* 66, 186–187 (1973) by L. L. Sower, K. W. Vick, and J. S. Long. Air from an outside source was filtered with activated charcoal and introduced into the tubes at 1 liter/min. Light for observations was provided from below by an even, diffuse background illumination of 0.5 lux. A 5% sucrose solution on a cotton wick was provided ad libitum at the downwind end of the tube. All assays utilized 10 males/tube. Four hours prior to assay, males at least one day old were added to the tubes for replacement of dead or moribund individuals. The males were held on a 16:8 LD regime at 22° C and assays were conducted between 3.5 and 4.5 hours of scotophase. Synthetic chemicals were dispensed in 10 to 100 $\mu$l of Skellysolve B onto a 1 × 2 cm piece of filter paper. Each cage was observed for spontaneous activity for 1 min, followed by 1 min of observation after the chemical sample was introduced into the airstream. The key male behavioral responses scored were wing vibration and positive upwind orientation, defined as the relative increase in the number of males within 15 cm of the upwind end of the tube at the termination of the 1 min observation period. Use of a criterion of activation was precluded by the high level of spontaneous walking.

Field tests were conducted in potato fields at the University of California Field Station, Moreno, Calif. The experimental area was a 0.5 acre potato field in which vines had been previously knocked down and the ground rolled; tubers were still in the ground. The Pherocon IC traps (Zoecon Corp.) were deployed at a height of 0.3 m above the ground in a randomized complete block design with 5 replicates. Blocks were separated by 8 m and traps within a block by 15 m. At 4-day intervals, the trapped males were counted, the virgin females replaced, and the traps within each block rerandomized. The moths captured were totaled and the pooled data subjected to analysis of variance. The means followed by the same letter are not significantly different at the 1% or the 5% level as determined by Duncan's multiple range test. The test chemicals were placed in polyethylene caps (OS-6 natural polyethylene closures, Scientific Products) or in rubber septa (5 × 9 mm rubber stoppers, sleeve-type, Arthur H. Thomas Co.) along with 10% antioxidant, Universal Oil Products 688 (N-phenyl-N'-2-octyl-p-phenylenediamine).

(B) Identifying the Active Compounds in the Pheromone.

Female potato tuberworm gland extract (ca. 60 FE) was injected onto the OV-1 column at 160° C and the effluent was collected in 1-min fractions for 20 min. EAG analysis of the collected fractions using male potato tuberworm moth antennae showed a minor area of activity at 5–6 min (1.6 mv) and a minor area of activity at 8–9 min (3.2 mv) and 9–10 min. (2.1 mv) compared to all other fractions at less than 1 mv. Retention times of tridecyl alcohol and acetate standards were 5.2 and 9.25 min, respectively. These areas of activity were reproducible on all female gland extract analyzed.

Extract from batches of ca. 1000 female glands typically was purified by collection from the high pressure liquid chromatography column (fractions assayed by EAG to show activity in the fraction eluting in 20–24 min), and then collection from the OV-1 column. Alternatively, the extract from ca. 1000 female glands was collected from the SE-30 preparative column at 200° C. A typical collection showed EAG activity at 5–6 min (3.2 mv) and at 7–9 min (5.2 mv).

Major activity.

The major EAG activity was shown to be due to a compound(s) possessing an acetate group by saponification and reacteylation. An aliquot of purified extract was collected from OV-1 at 150° C to give EAG activity (3.9 mv) at 7–8 min. Treatment with 5% methanolic KOH followed by injection on the OV-1 column showed slight activity (0.4 mv) at 5–6 min, but none at the longer retention times (tridecyl alcohol and acetate were 5.1 and 8.1 min, respectively). Reacetylation of the 5–6 min fraction and then injection onto the OV-1 column showed the activity (2.0 mv) restored in the 7–8 min fraction.

The acetate fraction collected from OV-1 was collected from the CHDMS column at 145° C to give high activity (3.5 mv) at 15–16 min (tridecyl acetate was 12.9 min). This component had a longer retention time than all monounsaturated 13-carbon acetates, suggesting the possibility of 2 or more double bonds. A chemical ionization mass spectrum of the purified compound supported a doubly-unsaturated 13-carbon acetate structure. The important ions occurred at m/e (relative abundance) 237(2) M-1, 179(64) [M + 1]–60, 177(20), 163(10), 137(22), 111(12), 109(60), 97(70), 95(100), 83(20), and 81(38).

Micro-ozonolysis of the active component collected from OV-1 and CHDMS columns produced one fragment with retention time (5.1 min) similar to that of hexanal (4.8 min) on the Carbowax 20M (programmed from 60° C with a 5-min hold to 200° C at 5°/min). A small peak was also visible at the retention time (20.1 min) of 4-acetoxybutanal. These data are consistent with the structure 4,7-tridecadienyl acetate.

Electroantennogram studies with a series of monounsaturated 10-, 12-, 13- and 14-carbon alcohol, acetates and aldehydes showed that the male antennae were the most responsive to the 12- and 13-carbon acetate series. The two compounds eliciting the best responses in the 12-, 13- and 14-carbon acetate series were the trans-4 and the cis-7 standards. These data suggested trans-4, cis-7-tridecadienyl acetate as a component.

(C) Synthesis of trans-4,cis-7-tridecadienyl acetate (t4,c7-13:Ac).

The synthetic route followed is outlined in FIG. 1. 4-Pentyn 1-01 was converted to the mixed acetal I with ethyl vinyl ether as described in *J. Org. Chem* 37, 1947–1950 (1972) by P. E. Eaton, G. F. Cooper, R. C. Johnson and R. H. Mueller to protect the alcohol function. Treatment of I with n-butyllithium gave the lithium salt which reacted with paraformaldehyde to give the propargylic alcohol II in 71% yield. Steroselective reduction of II with lithium aluminum hydride in tetrahydrofuran under the reflux gave the trans allylic alcohol III in 84% yield. The alcohol III was converted to the desired allylic chloride IV in 93% yield by the method of Collington and Meyers *J. Org. Chem* 36, 3044–3045 (1971) (using methanesulfonyl chloride, lithium chloride, and 2, 4, 6-trimethylpyridine). The formation of IV proceeded without any detectable rearrangement or loss of sterochemistry and without attack on the acid-sensitive acetal protecting group.

Coupling of the allylic chloride IV with the acetylenic Grignard reagent 1-heptynyl-1-magnesium bromide (prepared from 1-heptyne and ethylmagnesium bromide in tetradydrofuran under reflux) was achieved by heating the two reactants in tetrahydrofuran under reflux in the presence of a catalytic quantity of cuprous chloride as described in *Preparative Acetylenic Chemistry*, p 30 by L. Brandsman, published by Elsevier Publishing Co., Amsterdam (1971). Hydrolysis of the crude reaction product V with trichloroacetic acid gave the alcohol VI, which was crystallized from pentane at −74° C and then distilled to give pure eneyne alcohol VI (98.8% pure by GLC analysis) in 60% yield. Careful partial hydrogenation of VI at 0° over Lindlar catalyst in hexane containing synthetic quinoline gave VII, which was acetylated to yield pure trans-4, cis-7-tridecadienyl acetate VIII (98% purity by GLC analysis) in 16.9% overall yield from 4-pentyn-1-01.

The acetate VIII had retention times on OV-1 and CHDMS columns identical to those of the pheromone component. The mass spectra (chemical ionization) were also identical and obtained at the same retention times from the GC-mass spectrometer.

(D) Testing the Male Behavioral Responses

Minor Activity - The material with some EAG activity and eluting earlier than the acetate component was collected from the OV-1 or SE-30 columns as described above. Material collected at 4–5 min from the OV-1 column at 160° C was treated with acetyl chloride and reinjected on the OV-1 column to give good antennal responses (4.0 mv) at 8–9 min (tridecyl acetate, 8.0 min) and none at the original 4–5 min fraction. The acetylated material on the CHDMS column had a retention time identical to the acetate VIII. This suggested that the original material with some EAG activity was the corresponding alcohol VII. It is possible that this alcohol is either part of the pheromone system or just a precursor in the gland.

Laboratory Behavioral Assays.

Laboratory behavioral tests with the acetate VIII showed that this component elicited wing fanning and upwind orientation at 10, 100, and 1000 ng (Table I, test A). The corresponding alcohol VII did not evoke any wing fanning or upwind orientation at 10, 100, or 1000 ng and in combination with the acetate VIII suppressed wing fanning and upwind orientation (Table 1, test B).

TABLE 1

| Treatment | Male bioassay of P. operculella | | | |
|---|---|---|---|---|
| | % wing vibration | C.I.* | % orientation | C.I.* |
| Test A | | | | |
| Spontaneous activity | 0 | 0–3 | — | — |
| 10 ng t4,c7-13:Ac | 21 | 15–28 | 33 | 26–39 |
| 100 ng t4,c7-13:Ac | 53 | 45–61 | 76 | 70–82 |
| 1000 ng t4,c7-13:Ac | 52 | 44–60 | 84 | 79–89 |
| Test B | | | | |
| Spontaneous activity | 0 | 9–5 | — | — |
| 10 ng t4,c7-13:Ac | 52 | 41–63 | 52 | 38–66 |
| 10 ng t4,c7-13:Ac + 10 ng t4,c7-13:OH | 22 | 13–33 | 7 | 2–18 |
| 10 ng t4,c7-13:Ac + 100 ng t4,c7-13:OH | 11 | 5–20 | 8 | 3–18 |
| 10 ng t4,c7-13:Ac + 500 ng t4,c7-13:OH | 28 | 18–39 | 9 | 3–20 |

*95% confidence interval; 18 replicates for test A and 8 replicates for test B

Field Tests

Synthetic VIII, t4,c7–13:Ac, was tested in the field for attractancy activity. In the first test treatments were (1) 2 mg VIII in a polyethylene cap, (2) 100 μg VIII on a rubber septum, (3) 10 μg VIII on a rubber septum, (4) 3 virgin females, and (5) unbaited traps. In this test, the synthetic chemical in treatments 1 and 2 proved to be active, but not as attractive as the females: x̄ were 11.2(b), 11.4(b), 3.8(c), 20.6(a), respectively, compared to 1.0(c) for the unbaited traps (significance at the 1% level).

The next test was designed to test effects of the alcohol VII on attractancy. Treatments consisted of 100 μg acetate VIII on a rubber septum and (1) no additional chemical, (2) 100 μg alcohol VII added, (3) 30 μg VII added, and (4) 10 μg VII added, as well as treatments with (5) 300 μg acetate VIII on a rubber septum, (6) 3 virgin females, and (7) unbaited traps. In this test the addition of the alcohol VII did not appear to increase trap catch, but the treatment with 300 μg acetate VIII was as competitive as the females: x̄ were 1.6(b), 0.0(b), 0.6(b), 0.0(b), 6.2(a), 5.8(a), and 0.0(b), respectively (significance at the 5% level.

What is claimed is:

1. In a method for control of the male potato tuberworm moth, *Phthorimea operculella*, by subjecting said moth to a sex attractant in an amount sufficient to attract the moth to a particular location, the improvement which comprises the use as said sex attractant of an effective amount of trans-4, cis-7-tridecadienyl acetate.

2. The method of claim 1 wherein said sex attractant is inserted into an insect trap which is located in an area which it is desired to protect from said moth.

3. The method of claim 1 wherein said sex attractant is employed to permeate the air over an area which it is desired to protect from said moth.

* * * * *